United States Patent
Simons et al.

(10) Patent No.: US 11,101,481 B2
(45) Date of Patent: Aug. 24, 2021

(54) SOLID STATE GLUCOSE-POWERED MICRO FUEL CELL

(71) Applicant: Massachusetts Institute of Technology, Cambridge, MA (US)

(72) Inventors: Philipp Simons, Cambridge, MA (US); Jennifer L.M. Rupp, Cambridge, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 503 days.

(21) Appl. No.: 15/901,732

(22) Filed: Feb. 21, 2018

(65) Prior Publication Data

US 2019/0260053 A1 Aug. 22, 2019

(51) Int. Cl.
| | |
|---|---|
| *A61B 5/145* | (2006.01) |
| *A61B 5/1486* | (2006.01) |
| *A61M 5/172* | (2006.01) |
| *H01M 16/00* | (2006.01) |
| *H01M 4/92* | (2006.01) |
| *H01M 8/1009* | (2016.01) |
| *H01M 8/1016* | (2016.01) |
| *H01M 8/16* | (2006.01) |
| *H01M 8/124* | (2016.01) |

(52) U.S. Cl.
CPC ......... *H01M 8/1009* (2013.01); *A61B 5/1486* (2013.01); *A61B 5/14532* (2013.01); *A61M 5/1723* (2013.01); *H01M 4/92* (2013.01); *H01M 8/1016* (2013.01); *H01M 16/006* (2013.01); *A61B 2560/0214* (2013.01); *A61M 2205/8206* (2013.01); *A61M 2230/201* (2013.01); *H01M 8/16* (2013.01); *H01M 2008/1293* (2013.01); *H01M 2250/30* (2013.01); *H01M 2300/0071* (2013.01)

(58) Field of Classification Search
CPC .............................. A61B 5/14; A61M 5/1723
See application file for complete search history.

(56) References Cited

U.S. PATENT DOCUMENTS

| | | | |
|---|---|---|---|
| 3,837,339 A | * | 9/1974 | Aisenberg ............ A61B 5/0002 604/504 |
| 8,507,147 B2 | | 8/2013 | Mofakhami |
| 2007/0042377 A1 | | 2/2007 | Gao et al. |
| 2007/0048577 A1 | | 3/2007 | Ringeisen et al. |
| 2007/0117005 A1 | | 5/2007 | Fuglevand et al. |

(Continued)

FOREIGN PATENT DOCUMENTS

| | | |
|---|---|---|
| JP | 2012054116 A | 3/2012 |
| WO | 2016190813 A1 | 12/2016 |

OTHER PUBLICATIONS

Barton, S., et al.—"Enzymatic Biofuel Cells for Implantable and Microscale Devices," Chem. Rev., vol. 104, pp. 4867-4886, 2004.

(Continued)

*Primary Examiner* — Haroon S. Sheikh
(74) *Attorney, Agent, or Firm* — Nutter McClennen & Fish LLP

(57) ABSTRACT

The present application provides a new type of glucose fuel cell in which a layer of proton-conducting metal oxide is interposed between the anode and cathode electrodes. Such metal oxides can serve in the form of thin-layer fuel cell membrane materials for novel, all-solid state fuel cell designs.

36 Claims, 10 Drawing Sheets
(10 of 10 Drawing Sheet(s) Filed in Color)

(56) References Cited

U.S. PATENT DOCUMENTS

| | | | |
|---|---|---|---|
| 2009/0087712 A1 | 4/2009 | Huang et al. | |
| 2013/0224632 A1* | 8/2013 | Roumi | H01M 2/1646 |
| | | | 429/516 |
| 2014/0211370 A1 | 7/2014 | Seymour et al. | |
| 2014/0342247 A1 | 11/2014 | Sarpeshkar et al. | |
| 2016/0114038 A1* | 4/2016 | Mair | H01M 8/1097 |
| | | | 424/489 |

OTHER PUBLICATIONS

Bleszynski, P.A., et al.—"Current State and Future Perspectives of Energy Sources for Totally Implantable Cardiac Devices," ASAIO J, vol. 16, Issue 6, pp. 639-645, Nov./Dec. 2016.

Chueh, W.C., et al.—"High Electrochemical Activity of the Oxide Phase in Model Ceria-Pt and Ceria-Ni Composite Anodes," Nat Mater, vol. 11, No. 2, pp. 155-61, 2012.

Do, U.P., et al.—"Thin Film Nanoporous Electrodes for the Selective Catalysis of Oxygen in Abiotically Catalyzed Micro Glucose Fuel Cells," Journal of Materials Science, vol. 51, Issue 19, pp. 9095-9107, 2016.

Fishman, J.H., et al.—"Electrodeposited Selective Catalysts for Implantable Biological Fuel Cells," Electrochemical Bioscience and Bioengineering, pp. 199-210, 1973.

Gougis, M., et al.—"Simultaneous Deposition of Cerium Oxide and Gold Nanostructures-Characterization and Analytical Properties Toward Glucose Electro-Oxidation and Sensing," RSC Adv., vol. 4, Issue 75, pp. 39955-39961, 2014.

Gregori, G., et al.—"Proton Conduction in Dense and Porous Nanocrystalline Ceria Thin Films," Advanced Functional Materials, vol. 23, pp. 5861-5867, 2013.

International Searching Authority—International Search Report and Written Opinion for International Application No. PCT/US2019/018566, dated Apr. 15, 2019, 16 pages.

Kerzenmacher, S., et al.—"Energy Harvesting by Implantable Abiotically Catalyzed Glucose Fuel Cells," Journal of Power Sources, vol. 182, No. 1, pp. 1-17, 2008.

Kerzenmacher, S., et al.—"An Abiotically Catalyzed Glucose Fuel Cell for Powering Medical Implants: Reconstructed Manufacturing Protocol and Analysis of Performance," Journal of Power Sources, vol. 182, Issue 1, pp. 66-75, Jul. 15, 2008.

Kerzenmacher, S., et al.—"Raney-Platinum Film Electrodes for Potentially Implantable Glucose Fuel Cells. Part 1: Nickel-Free Glucose Oxidation Anodes," Journal of Power Sources, vol. 195, No. 19, pp. 6516-6523, 2010.

Kerzenmacher, S., et al.—"Raney-Platinum Film Electrodes for Potentially Implantable Glucose Fuel Cells. Part 2: Nickel-Free Glucose Oxidation Anodes," Journal of Power Sources, vol. 195, No. 19, pp. 6524-6531, 2010.

Kerzenmacher, S., et al.—"A Potentially Implantable Glucose Fuel Cell with Raney-Platinum Film Electrodes for Improved Hydrolytic and Oxidative Stability," Journal of Power Sources, vol. 196, No. 3, pp. 1264-1272, 2011.

Kloke, A., et al.—"A Single Layer Glucose Fuel Cell Intended as Power Supplying Coating for Medical Implants," Fuel Cells, vol. 11, No. 2, pp. 316-326, 2011.

Oh, T., et al.—"Proton Conductivity of Columnar Ceria Thin-Films Grown by Chemical Vapor Depression," Phys. Chem., Chem. Phys., vol. 15, pp. 2466-2472, 2013.

Oncescu, V., et al.—"High Volumetric Power Density, Non-Enzymatic, Glucose Fuel Cells," Sci Rep, vol. 3, 6 pages, 2013.

Rapoport, B.I., et al.—"A Glucose Fuel Cell for Implantable Brain-Machine Interfaces," PLoS ONE, vol. 7, Issue 6, 15 pages, Jun. 2012.

Shi, Y., et al.—"The Effect of Mechanical Twisting on Oxygen Ionic Transport in Solid-State Energy Conversion Membranes," Nat Mater, vol. 14, No. 7, pp. 721-7, 2015.

Shirpour, M., et al.—"On the Proton Conductivity in Pure and Gadolinium Doped Nanocrystalline Cerium Oxide," Phys. Chem. Chem. Phys., vol. 13, pp. 937-940, 2011.

Sone, Y., et al.—"Proton Conductivity of Nafion 117 as Measured by a Four-Electrode AC Impedance Method," Journal of the Electrochemical Society, vol. 143, No. 4, pp. 1254-1259, 1996.

Song, et al.—"Ceria promoted Pd/C catalysts for glucose electrooxidation in alkaline media", Applied Catalysis B: Enviornmental, Elsevier, Amsterdam, NL, vols. 176-177, pp. 233-239, Oct. 2015, available online Apr. 1, 2015.

* cited by examiner

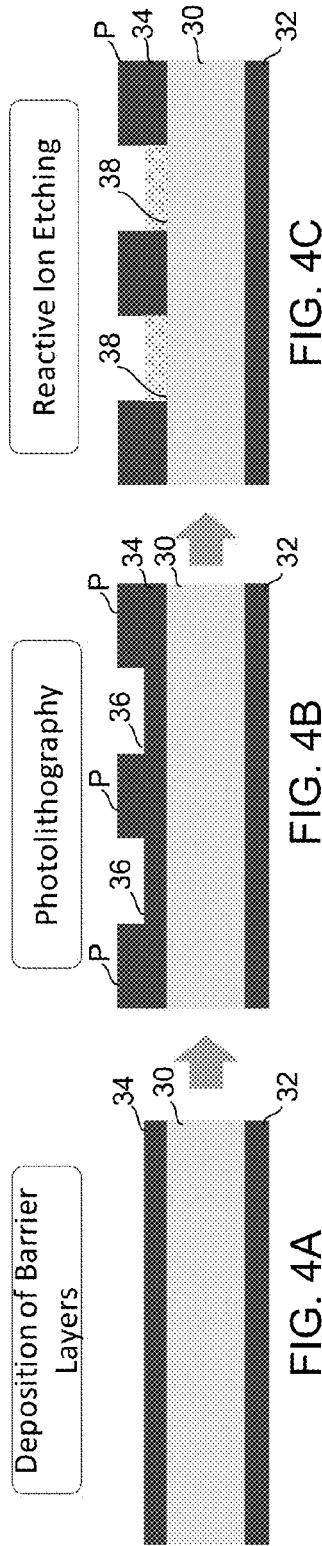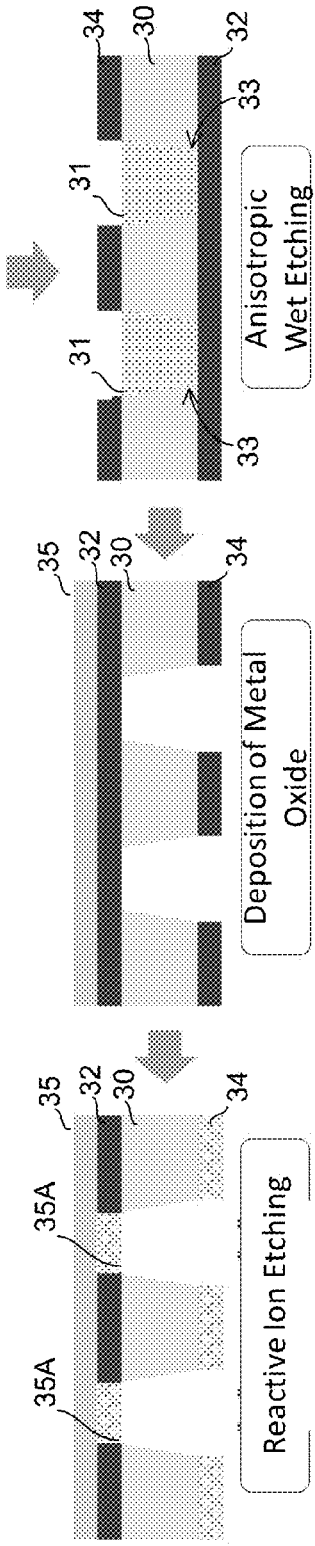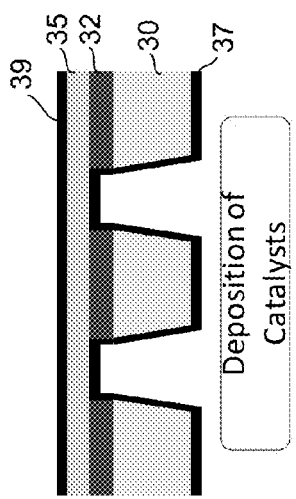

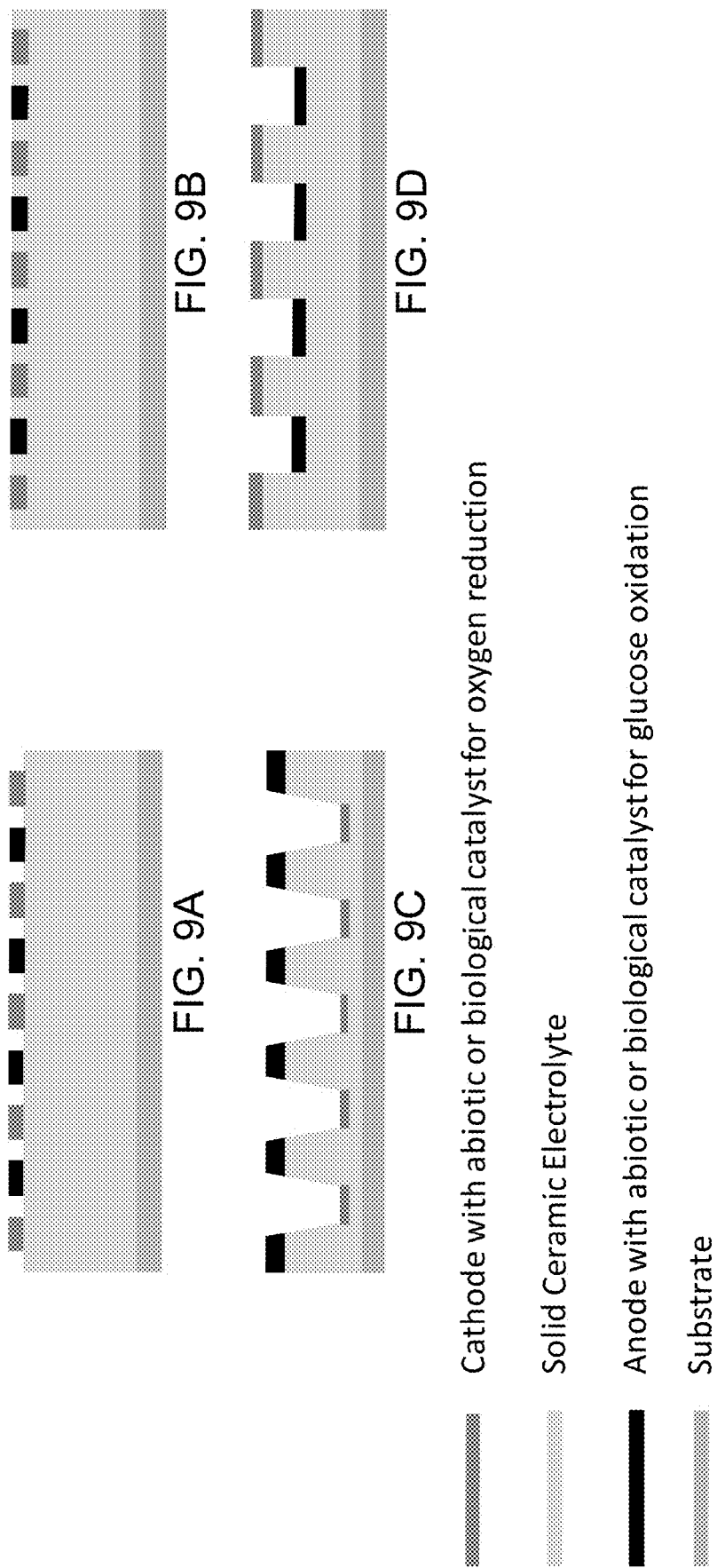

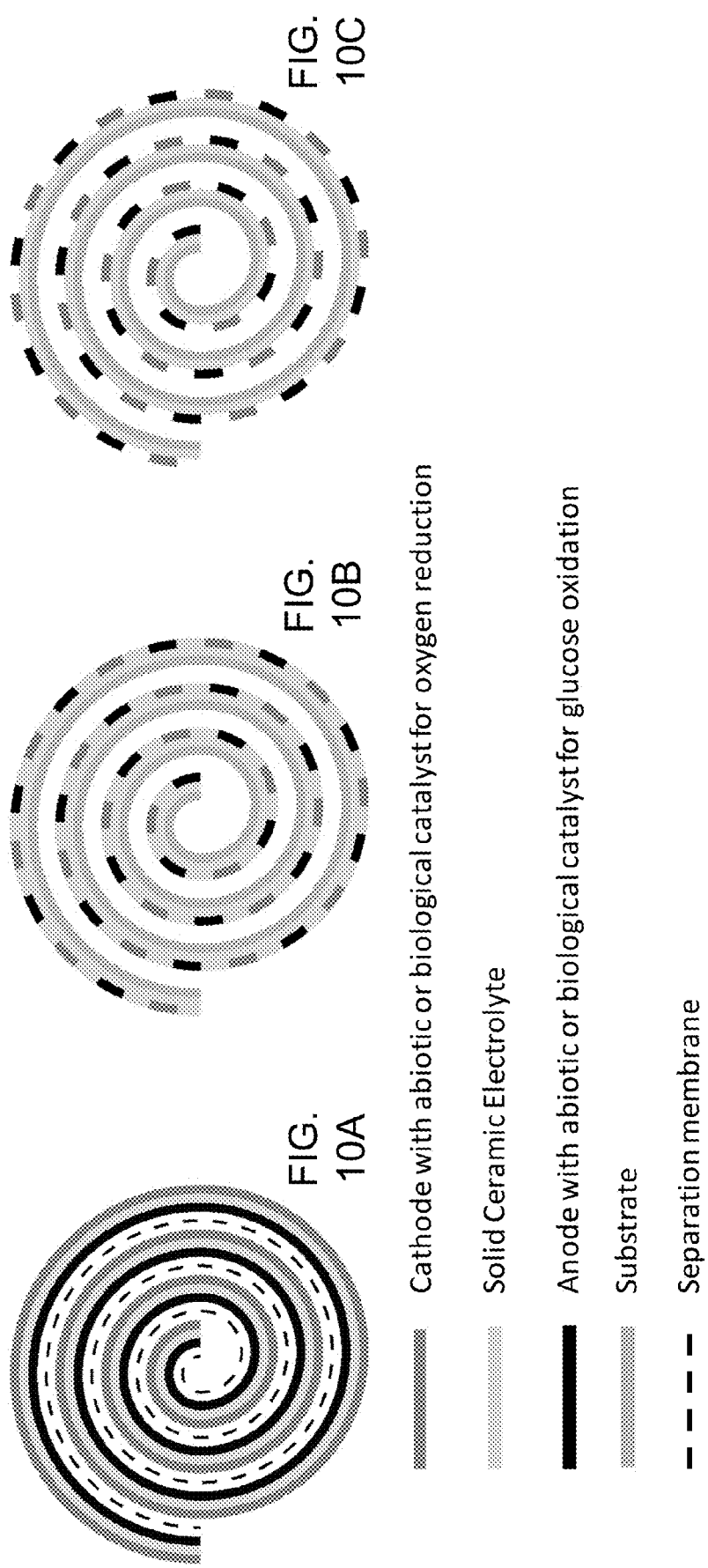

SOLID STATE GLUCOSE-POWERED MICRO FUEL CELL

TECHNICAL FIELD

The present invention relates to glucose fuel cells and more particularly to solid state fuel cells featuring metal oxide electrolytes.

BACKGROUND ART

Reference may be made to the following:
[1] Bleszynski, P. A., et al., *Current State and Future Perspectives of Energy Sources for Totally Implantable Cardiac Devices*. ASAIO J, 2016. 62(6): p. 639-645;
[2] Kerzenmacher, S., et al., *Energy harvesting by implantable abiotically catalyzed glucose fuel cells*. Journal of Power Sources, 2008. 182(1): p. 1-17;
[3] Scott Calabrese Barton, Josh Gallaway, and P. Atanassov, *Enzymatic Biofuel Cells for Implantable and Microscale Devices*. Chem. Rev., 2004(104): p. 4867-4886;
[4] Shirpour, M., et al., *On the proton conductivity in pure and gadolinium doped nanocrystalline cerium oxide*. Phys Chem Chem Phys, 2011. 13(3): p. 937-40;
[5] Gregori, G., M. Shirpour, and J. Maier, *Proton Conduction in Dense and Porous Nanocrystalline Ceria Thin Films*. Advanced Functional Materials, 2013. 23(47): p. 5861-5867.
[6] Oh, T. S., et al., *Proton conductivity of columnar ceria thin films grown by chemical vapor deposition*. Phys Chem Chem Phys, 2013. 15(7): p. 2466-72;
[7] Sone, Y., P. Ekdunge, and D. Simonsson, *Proton Conductivity of Nafion 117 as Measured by a Four-Electrode AC Impedance Method*. Journal of The Electrochemical Society, 1996. 143(4): p. 1254-1259;
[8] Shi, Y., et al., *The effect of mechanical twisting on oxygen ionic transport in solid-state energy conversion membranes*. Nat Mater, 2015. 14(7): p. 721-7;
[9] Rapoport, B. I., J. T. Kedzierski, and R. Sarpeshkar, *A glucose fuel cell for implantable brain-machine interfaces*. PLoS ONE, 2012. 7(6);
[10] Fishman, J. H. and J. F. Henry, *Electrodeposited Selective Catalysts for Implantable Biological Fuel Cells*. Electrochemical Bioscience and Bioengineering, 1973: p. 199-210;
[11] Kerzenmacher, S., et al., *Raney-platinum film electrodes for potentially implantable glucose fuel cells. Part 1: Nickel-free glucose oxidation anodes*. Journal of Power Sources, 2010. 195(19): p. 6516-6523;
[12] Kerzenmacher, S., et al., *Raney-platinum film electrodes for potentially implantable glucose fuel cells. Part 2: Glucose-tolerant oxygen reduction cathodes*. Journal of Power Sources, 2010. 195(19): p. 6524-6531;
[13] Kerzenmacher, S., et al., *A potentially implantable glucose fuel cell with Raney-platinum film electrodes for improved hydrolytic and oxidative stability*. Journal of Power Sources, 2011. 196(3): p. 1264-1272;
[14] Kloke, A., et al., *A Single Layer Glucose Fuel Cell Intended as Power Supplying Coating for Medical Implants*. Fuel Cells, 2011. 11(2): p. 316-326;
[15] Oncescu, V. and D. Erickson, *High volumetric power density, non-enzymatic, glucose fuel cells*. Sci Rep, 2013. 3: p. 1226;
[16] Chueh, W. C., et al., *High electrochemical activity of the oxide phase in model ceria-Pt and ceria-Ni composite anodes*. Nat Mater, 2012. 11(2): p. 155-61;
[17] Gougis, M., et al., *Simultaneous deposition of cerium oxide and gold nanostructures-characterization and analytical properties toward glucose electro-oxidation and sensing*. RSC Adv., 2014. 4(75): p. 39955;
[18] Kerzenmacher, S., et al., *An abiotically catalyzed glucose fuel cell for powering medical implants: Reconstructed manufacturing protocol and analysis of performance*. Journal of Power Sources, 2008. 182(1): p. 66-75; and
[19] Do, U. P., et al., *Thin film nanoporous electrodes for the selective catalysis of oxygen in abiotically catalysed micro glucose fuel cells*. Journal of Materials Science, 2016. 51(19): p. 9095-9107.

One present challenge in implantable medicine is that the miniaturization of biomedical devices and implants such as sensors, pacemakers and bioelectronics requires small, powerful and long-lasting power sources. Traditionally, batteries are used to power implants such as sensors or pacemakers; however, those devices are based on rather "bulky" setups and require replacement by surgery on the patient due to their limited battery life-time every 7-10 years. [1] In particular, batteries store their energy inside the active components, i.e., the electrodes, and therefore increasing the energy content of a battery means that the size of the battery needs to be increased, as well. In contrast, fuel cells are not limited by a specific storage capacity as a battery if they use chemical energy sources readily available in the bloodstream, such as glucose. As illustrated in FIG. 1, the glucose undergoes oxidation at the anode of the fuel cell, to produce, for example, gluconic acid, and the resulting protons migrate through the electrolyte to the cathode, while the electrons travel through an external circuit to power an electric device. At the cathode, oxygen also from the bloodstream is reduced to water. This makes glucose fuel cells candidates for small scale, long term implantable power sources, and explains the increased research efforts in recent years. [2, 3]

Despite recent progress on glucose fuel cells, enzymatic and microbial fuel cells suffer still from low power output due to the sluggish charge kinetics of electroactive microorganisms. Such fuel cells are based on biological catalysts such as enzymes or bacteria. The enzymes or bacteria need to be immobilized in order to adhere to the electrode surface of a fuel cell, and at the same time good conductivity of charge carriers (electrons and protons) away from the catalytically active sites has to be established through a hydrophylic polymer membrane. These problems have not been solved adequately so far. In addition, the power range and long term stability of such enzyme-based fuel cells tends to be limited.

Alternatively, abiotic glucose fuel cells can operate on the catalysis of abiotic reactions, in the absence of living organisms or enzymes as fuel cell constituents. Using abiotical solid state catalysts may have the potential to solve the key shortcomings of biological catalysts of enzymatic and microbial fuel cells: for most solid state catalysts such as metals or metal oxides, catalyst adhesion and sufficient charge transport do not pose significant problems. However, biological catalysts are complex molecules or organisms, which have perfected their catalytic activity and selectivity through millions of years of evolution. As a result, finding abiotic catalysts with similar activity and selectivity as biological ones can be a challenge.

Traditionally, biological and abiotical cells alike rely on proton conducting electrolytes that are primarily based on polymers such as Nafion. The typical thickness of a Nafion-based electrolyte is in the range of tens of micrometers. For example, Rapoport et al. have described a fuel cell based on the "fuel depletion" design. [9] In their fuel cell system, a cathode made up of a mesh of single walled carbon nanotubes (CNTs) surrounds a proton conducting polymer membrane and a Raney-type platinum anode. Through the design, the anode is completely sealed off from the physiological fuel mixture, and only the cathode is in direct contact with the fuel containing both glucose and oxygen. The reported design makes use of the selectivity of CNTs towards the reduction of oxygen under the presence of glucose, thereby depleting the oxygen at the cathode side, and rendering only glucose present on the anode side. The device is integrated on a silicon chip, which is the basis for all modern electronic devices, thus creating potential for integration into bioelectronic devices. However, the Nafion membrane employed limits the potential for downscaling of the electrolyte.

SUMMARY OF THE EMBODIMENTS

In accordance with one embodiment, a device comprises a glucose fuel cell comprising an anode configured to oxidize glucose; a cathode configured to reduce an oxidant, and a proton-conducting metal oxide electrolyte interposed between the anode and cathode.

In various alternative embodiments, the metal oxide may include $CeO_2$ alone or doped with at least one rare earth element. Additionally or alternatively, the metal oxide may include a perovskite oxide of the form $ABO_3$, such as, for example, an oxide selected from group consisting of $SrTiO_3$, $SrZrO_3$, $BaCeO_3$, $BaZrO_3$, $BaTiO_3$, $BaTbO_3$, $BaThO_3$, $SrCeO_3$, $CaZrO_3$, $LaScO_3$, $LaErO_3$, $KTaO_3$, and combinations thereof. Such metal oxides may be doped with an element selected from the group consisting of Y, Sc, In, Gd, Sr, Hf, Ce, Ca, Zr, Sm and combinations thereof. The metal oxide may be hydrated. The metal oxide material may be selected from the group consisting of $SrCe_{1-x}Yb_xO_3$ (where x is from at least 0 to at most 1); $LaY_{1-x}Zn_xO_3$ (where x is from at least 0 to at most 1); $Sr_2(GaNb)O_6$; $Ba_3CaNb_2O_9$; and $ZrO_2$. Such metal oxides may be doped with at least one rare earth element. The metal oxide may be a biocompatible metal oxide. The metal oxide may be amorphous, polycrystalline, nanocrystalline or biphasic amorphous to nanocrystalline.

The electrolyte may have a thickness from at least 10 nm to at most 10 µm. The anode and cathode may be arranged in an in-plane configuration or in a cross-plane configuration. The glucose fuel cell may be in a folded or rolled-up configuration. A fluid comprising glucose may be contacted with the anode in order to generate electric current.

Oxidation of the glucose may be catalyzed by one or more of an abiotic catalyst, an enzyme, or a living cell. For example, oxidation of the glucose may be catalyzed by an abiotic catalyst selected from the group consisting of platinum, nanostructured platinum, platinum alloys, platinum-ruthenium, platinum-bismuth, platinum-tungsten, Raney-platinum, ceria-platinum, ceria-nickel, gold-platinum, gold-palladium, ceria-gold, rhodium, iridium, and combinations thereof. The metal oxide material may catalyze the oxidation of the glucose. The oxidant may include oxygen. Reduction of the oxidant may be catalyzed by one or more of a carbon nanotube supported catalyst, activated carbon, palladium, Raney-platinum, or silver.

The glucose fuel cell may be configured to oxidize glucose from a bodily fluid such as blood. The device may be configured to be implanted in a vertebrate. The device may further include an electrical storage device, such as a rechargeable battery, coupled to the glucose fuel cell for storage of electrical power from the glucose fuel cell. The device may further include a glucose sensor configured to output a glucose level signal based on a voltage of the glucose fuel cell. The glucose level signal may be related logarithmically to the voltage of the glucose fuel cell according to the Nernst equation. The device may further include a pump configured to pump at least one fluid based on the glucose level signal. The at least one fluid may include insulin.

In accordance with another set of embodiments, a method of manufacturing a glucose fuel cell comprises forming a proton conducting metal oxide layer on a first surface of a substrate, the metal oxide layer having a first metal oxide layer surface facing the substrate and a second metal oxide layer surface facing away from the substrate; etching a cavity on a second surface of the substrate to expose a portion of the first metal oxide layer surface; and one of: (a) forming an anodic electrode on a portion of the second metal oxide layer surface and forming a cathodic electrode on a portion of the first metal oxide layer surface; or (b) forming an anodic electrode on a portion of the first metal oxide layer surface and forming a cathodic electrode on a portion of the second metal oxide layer surface.

In various alternative embodiments, the metal oxide proton conducting layer may be formed according to one of a pulsed laser deposition process, a spray pyrolysis process, a reactive magnetron sputtering deposition process, or a radio frequency magnetron sputtering deposition process. The substrate may include a substrate layer and a first barrier layer formed on the substrate layer, and where the metal oxide layer is formed on the first barrier layer. Etching a cavity may involve forming a photoresist layer on the second barrier layer of a substrate having a first barrier layer on the first side of the substrate and a second barrier layer on the second side of the substrate; developing a portion of the photoresist layer according to a photolithographic process to expose a portion of the second barrier layer; applying a reactive ion etching process to the exposed portion of the second barrier layer, to expose a portion of the second side of the substrate; applying an anisotropic wet etch process to the exposed portion of the second side of the substrate, to expose a portion of the surface of the first barrier layer facing the substrate; and applying a reactive ion etching process to the exposed portion of the first barrier layer. Forming the cathode electrode may involve depositing a first abiotic catalyst and forming the anode electrode comprises depositing a second abiotic catalyst. The first and second barrier layers may be formed according to a low pressure chemical vapor deposition process.

Additional embodiments may be disclosed and claimed.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The foregoing features of embodiments will be more readily understood by reference to the following detailed description, taken with reference to the accompanying drawings, in which:

FIGS. 4A-4G include cross-sectional schematic representations of an exemplary method for manufacturing a miniaturized fuel cell in a cross-plane configuration, in accordance with one exemplary embodiment.

FIGS. 9A-9D include cross-sectional illustrations of some alternative in-plane and cross-plane glucose fuel cell configurations, in accordance with various exemplary embodiments of the present invention.

FIGS. 10A-10C include cross-sectional illustrations of some alternative rolled-up in-plane and cross-plane glucose fuel cell configurations, in accordance with various exemplary embodiments of the present invention.

It should be noted that the foregoing figures and the elements depicted therein are not necessarily drawn to consistent scale or to any scale. Unless the context otherwise suggests, like elements are indicated by like numerals.

DETAILED DESCRIPTION OF SPECIFIC EMBODIMENTS

Figure 1:
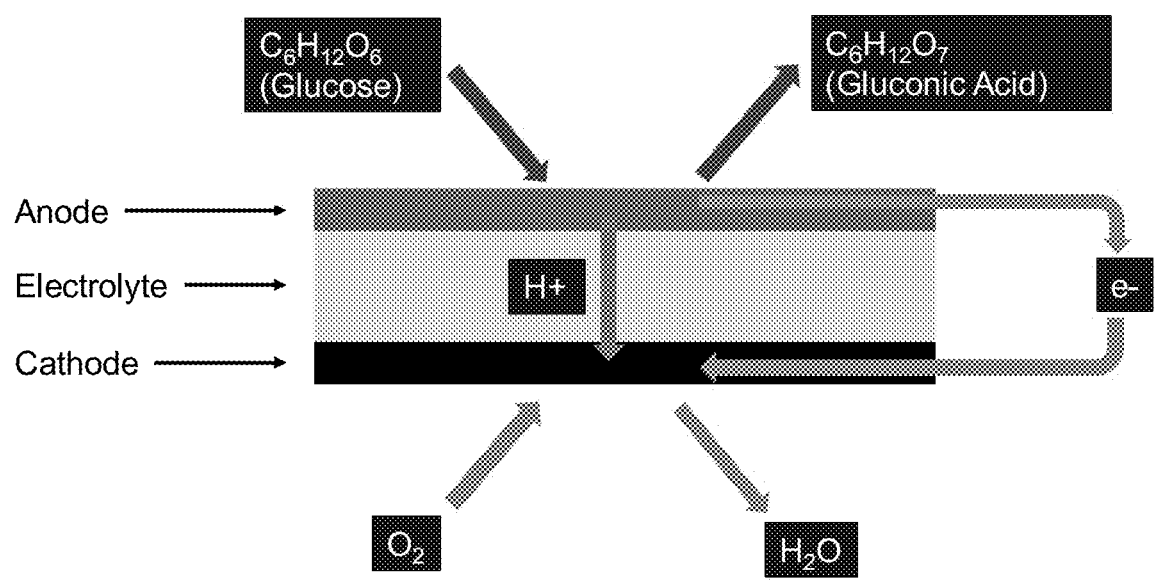
FIG. 1 is a cross-sectional schematic representation illustrating the reactions typically occurring in a glucose fuel cell as known in the art.

Definitions. As used in this description and the accompanying claims, the following terms shall have the meanings indicated, unless the context otherwise requires:

The "rare-earth elements" are cerium (Ce), dysprosium (Dy), erbium (Er), europium (Eu), gadolinium (Gd), holmium (Ho), lanthanum (La), lutetium (Lu), neodymium (Nd), praseodymium (Pr), promethium (Pm), samarium (Sm), scandium (Sc), terbium (Tb), thulium (Tm), ytterbium (Yb), and yttrium (Y).

A material doped with an element is not to be read as necessarily containing the element in its native state. For example, the doping element may be present as an ion, an oxide, or in other forms suitable to the application at hand.

The "electrolyte" of a cell is a composition of matter which is capable of conducting an ionic current. Typically, the electrolyte of a cell may be a liquid, paste, or solid. If the electrolyte is a paste, the cell is referred to as a dry cell; if the electrolyte is a solution, it is called a wet cell; if the electrolyte is a solid, it is called a solid-state cell.

A substrate is a structure on which another structure is formed. A particular structure may be formed on a substrate and may itself become a substrate for formation of another structure. In some situations, a substrate can include multiple structures and/or material layers. In some situations, a substrate can be flexible such as to allow for folded or rolled-up glucose fuel cells.

Components of the Fuel Cell.

In a first set of representative embodiments, the present application provides a new type of glucose fuel cell in which a layer of proton-conducting metal oxide is interposed between the anode and cathode electrodes. It has been found that certain types of metal oxide-based proton conductors are applicable to glucose fuel cells. As a result, such metal oxides can serve in the form of thin-layer fuel cell membrane materials for novel, all-solid state fuel cell designs. Most significantly, every decrease in the charge carrier transport path length by one order of magnitude correlates to a decrease of the ohmic resistance by the same factor. This means that in the case where the transport pathway is only a few hundred nanometers long compared to several tens of micrometers of a conventional Nafion membrane, the ohmic resistance is decreased 100-fold due to the reduced length scale.

This miniaturized technology is beneficial for a wide range of fuel-cell-powered devices including fuel-cell-powered devices that are fully or partially implantable. Furthermore, a miniaturized fuel cell design can be implemented on-chip together with sensor or bioelectronic devices using conventional semiconductor or Micro Electro Mechanical System (MEMS) fabrication techniques, or built into the casing of an implant. The glucose fuel cell can be used to power an on-chip device directly or can be used to energize an electrical storage device (e.g., a rechargeable battery or a capacitor) that in turn provides power to an on-chip device, thereby allowing for continued power when the amount of glucose in the glucose solution is low or nonexistent. Compared to classic Nafion-type polymer electrolytes, solid state metal oxide proton conductors give new perspective as they exhibit high protonic conductivity, can easily be downscaled in electrolyte thickness by 2-3 orders of magnitude, and are fully silicon compatible. Using a solid electrolyte material yields electrolytes at much smaller length scales, e.g., from about 10 μm down to only about 10 nm, as exemplified in the example fuel cell of FIG. 3 where the electrolyte is 240 nm thick. By reducing the charge carrier transport path length along the electrolyte to such a short distance, the ohmic resistance can be minimized, leading to significant performance enhancements in terms of power and energy density.

In addition, the smaller size ranges improve the potential for applications in implantable devices. A further benefit derived of this thin film approach based on all-solid state materials is that it allows for an implementation of the glucose fuel cell on-chip in a combined energy harvesting/sensor system. For example, the fuel cell technology of the present application may be put to work to measure glucose concentration in a glucose solution such as human blood or other bodily fluids by electrochemical means. For example, the glucose concentration can be measured through the electrochemical potential produced by the fuel cell, where the electrochemical potential depends on the glucose concentration in the glucose solution according to the Nernst equation:

$$E = E_0 + \frac{RT}{Z_i F} \ln \frac{c_1}{c_2}$$

where E is the cell potential, $E_0$ the standard cell potential, R the universal gas constant, T the temperature in Kelvins, F the Faraday constant, $Z_i$ the number of electrons transferred in the glucose oxidation reaction, $c_1$ the concentration of glucose, and $c_2$ the concentration of glucose oxidation product.

Therefore, a self-powered sensing device including a glucose fuel cell and a sensor that is powered directly or indirectly by the glucose fuel cell may be created in a single-chip design to autonomously measure the glucose concentration in the bloodstream of a patient or other fuel source. The sensor could be used to provide input to control an insulin pump to alleviate hyperglycemia. Also, as mentioned above, the glucose fuel cell can be used to power the on-chip sensor directly or can be used to energize an electrical storage device (e.g., a rechargeable battery or a capacitor) that in turn provides power to the on-chip sensor, thereby allowing for continued power when the amount of glucose in the glucose solution is low or nonexistent, for example, to generate an alarm or to operate a pump to introduce glucose into the blood to alleviate hypoglycemia.

Figure 2:
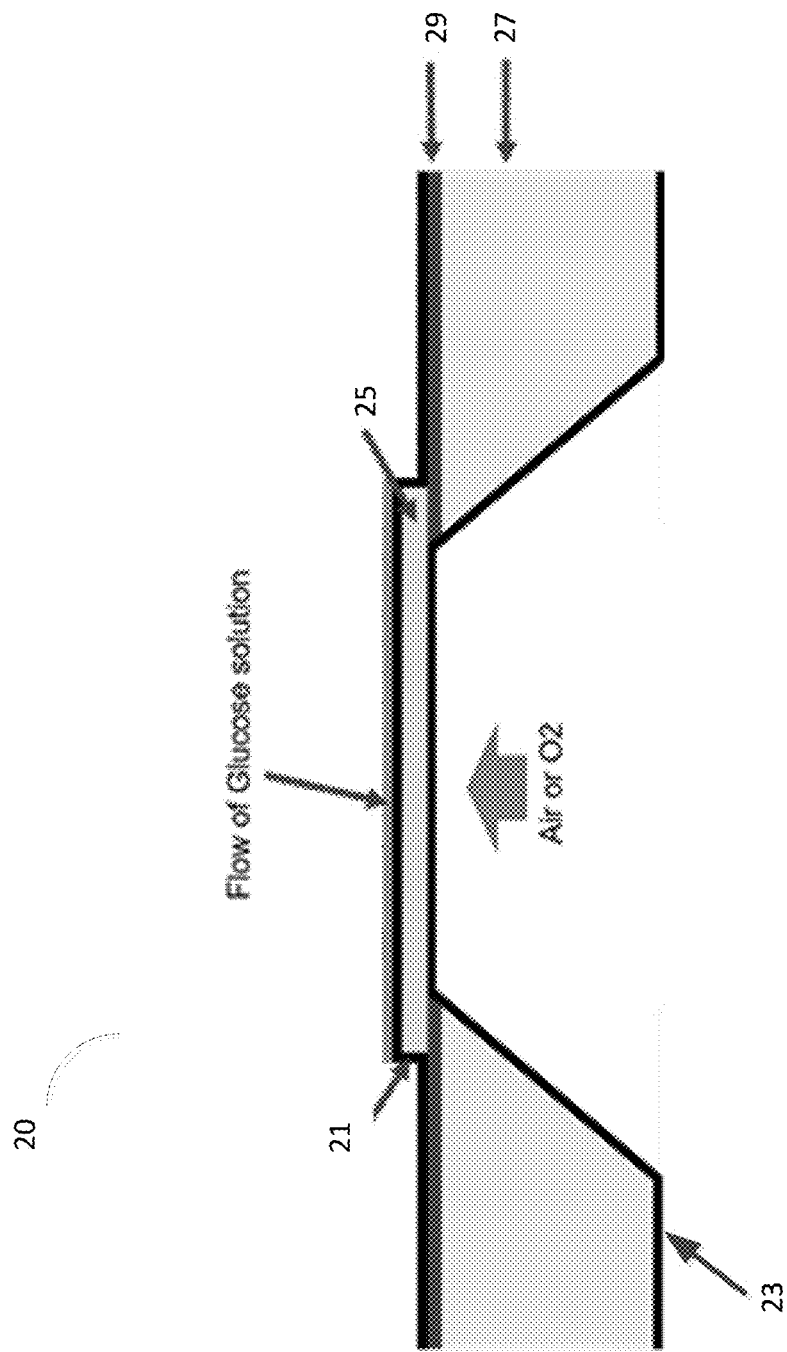
FIG. 2 is a cross-sectional schematic representation of an example glucose fuel cell in accordance with one exemplary embodiment.
Figure 3:
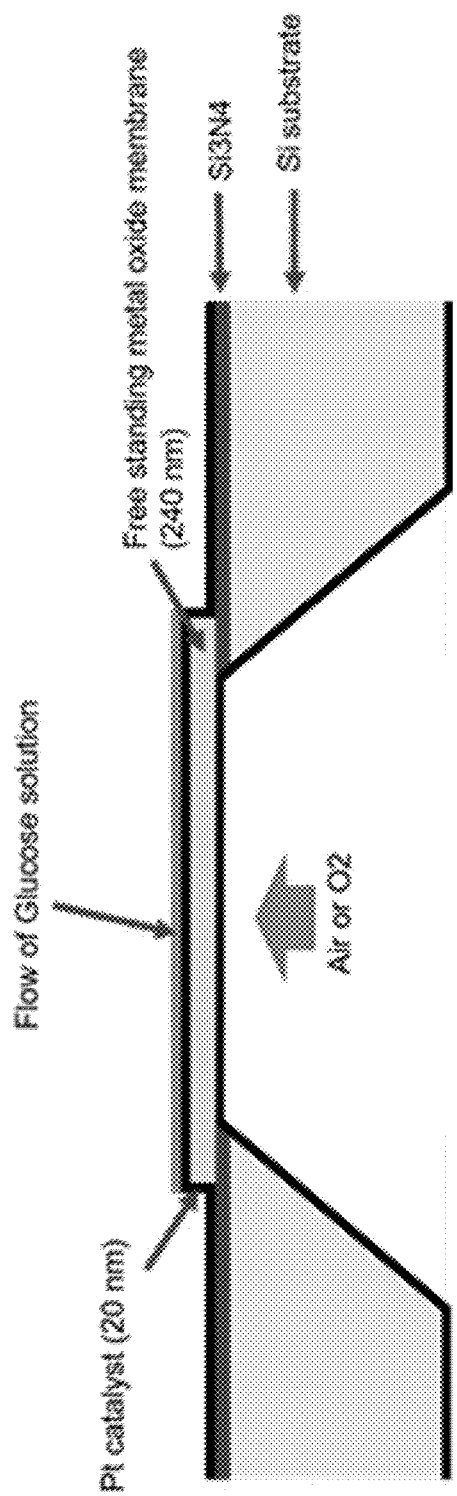
FIG. 3 is a cross-sectional schematic representation of one specific exemplary glucose fuel cell in accordance with one exemplary embodiment.

FIG. 2 is a cross-sectional schematic representation of an example glucose fuel cell 20 in accordance with one exemplary embodiment. Example glucose fuel cell 20 features anode 21, cathode 23 and proton-conducting electrolyte 25 interposed between anode 21 and cathode 23. In this example, structural support is provided by a substrate that includes substrate layer 27 over which a barrier layer 29 is laid. In one exemplary embodiment as depicted in FIG. 3, the substrate layer 27 is a silicon-based substrate layer (e.g., a silicon or polysilicon wafer) and the barrier layer 29 is $Si_3N_4$, although other types of substrate layer and barrier layer materials may be used in various alternative embodiments. In this exemplary embodiment, the anode includes a platinum-based catalyst, as discussed below, and the proton-conducting electrolyte 25 includes a metal oxide material exhibiting proton conductivity. For biomedical applications where the glucose is taken from blood or other bodily fluids of a patient, the electrolyte is preferably a biocompatible metal oxide that is proton-conducting at relatively low temperatures ranges, such as that of the human body. In some embodiments, the metal oxide material has a proton conductivity of at least $8 \cdot 10^{-5}$ S cm$^{-1}$ at temperatures in the range of 20° C. to 45° C. [6]

For example, the metal oxide may include hydrated ceria ($CeO_2$), optionally doped with one or more rare earth elements. Hydrated ceria is a known proton conductor at relatively low temperatures [5, 6], and is also known to be catalytically active by itself and in combination with other materials [16] The metal oxide material additionally or alternative may include a perovskite oxide of the form $ABO_3$ where A is typically an alkali or rare-earth element and B is typically a transition metal element, such as, for example, a perovskite oxide chosen from among $SrTiO_3$, $SrZrO_3$, $BaCeO_3$, $BaZrO_3$, $BaTiO_3$, $BaTbO_3$, $BaThO_3$, $SrCeO_3$, $CaZrO_3$, $LaScO_3$, $LaErO_3$, and $KTaO_3$, where the metal oxide may be hydrated to a certain extent and/or may be doped with one or more of Y, Sc, In, Gd, Sr, Hf, Ce, Ca, Zr, Sm and combinations thereof. Additional exemplary metal oxide materials include $SrCe_{1-x}Yb_xO_3$ (where x is from at least 0 to at most 1); $LaY_{1-x}Zn_xO_3$ (where x is from at least 0 to at most 1); $Sr_2(GaNb)O_6$; $Ba_3CaNb_2O_9$; and $ZrO_2$ optionally doped with one or more rare earth elements. Among these candidates, ceria is a known material to actually affect positively the treatment of cancer through a valence change reaction when locally placed in a human body. There are published scientific papers stating that it is biocompatible and also positive for cancerous cells therapy in the human body. Some other candidates, such as Ba and Sr, might be considered less desirable alternatives for certain embodiments, for example due to a concern that certain sub-isotopes of such materials could replace Ca in bones. In various exemplary embodiments, the metal oxide may be amorphous, polycrystalline, nanocrystalline or biphasic amorphous to nanocrystalline.

The anode is configured to oxidize glucose, for example by including a substance catalyzing the oxidation of glucose in the presence of water and yielding products such as gluconic acid. In some embodiments, the catalyst may be a living organism, for example a microbial cell, or a catalyst produced by a living organism, e.g., an enzyme such as a glucose oxidase. Also contemplated are embodiments where the catalyst is of abiotic origin. Using abiotical solid state catalysts has the potential to solve the key shortcomings of biological catalysts in enzymatic and microbial fuel cells. In this regard, it has been found that for most solid state, abiotic catalysts, catalyst adhesion and sufficient proton transport to the cathode do not pose significant problems in fuel cells where the proton-conducting electrolyte is a metal oxide.

One representative class of abiotic solid state catalysts is that of materials based on platinum and its alloys, including Raney-type platinum using sacrificial metals such as Al, Zn or Ni, platinum-ruthenium, platinum-bismuth, platinum tungsten, and gold-platinum. Other metals and alloys that are highly active for glucose oxidation include rhodium, iridium, and gold-palladium. Ceramic-metallic materials may also serve as glucose oxidation catalyst, including those based on ceria and noble or non-noble metals, for example ceria-gold, ceria-platinum, and ceria-nickel. In particular, ceria has been shown to be a catalytically active material in many energy conversion systems, and also a functional support in metal/metal oxide catalyst systems. [16, 17] Also contemplated is glucose oxidation catalyzed by nanostructured materials, e.g., nanostructured platinum, which would also be a biocompatible choice for insertion into the human body.

In the cathode part of the fuel cell, an oxidant is reduced to balance the reactions taking place in the anode. To this end, the cathode is configured to reduce the oxidant, for example, by inclusion of a reduction catalyst that is selective for the oxidant. In instances where the oxidant is oxygen, the selective catalyst may be carbon nanotubes (CNTs). [9] Activated carbon shows good selectivity towards the cathode reduction of oxygen in the presence of glucose. [18] Selective cathodes have also been made from palladium thin films deposited on nanoporous aluminum oxide. [19] Raney-platinum with aluminum as sacrificial element has also been reported for its activity as selective oxygen reduction catalyst [12,13], and a similar catalytic activity has been found in silver. [2]

It should be noted that the glucose fuel cell of FIG. 2 alternatively may be configured such that layer 21 is the cathode and layer 23 is the anode.

Manufacturing the Fuel Cell.

In some applications (such as certain applications where the fuel cell is part of an implantable device), the two fuel components, namely oxygen and glucose, may be mixed together in the same fluid such as blood or interstitial liquid and both the anode and the cathode of the fuel cell may be exposed to this fuel mixture. In order to operate a fuel cell based on this fuel mixture, there may be a need to separate the oxidant from the reductant or otherwise ensure that each electrode is selective to one component in the presence of the other. This may be achieved in a number of ways, such as, for example:

(1) In one configuration, a selective membrane is placed on the cathode that blocks the passage of glucose while allowing oxygen to reach the cathode. On the anodic side, one can take advantage of the relatively much higher glucose concentration relative to oxygen. As such, even a non-selective catalyst may be present on the anode electrode. In an analogous approach, the anode side may be fitted with a membrane that blocks the flow of oxygen while allowing the glucose to reach the anode;

(2) Another strategy is based on the so-called "fuel depletion design." In this configuration, a stacked layout is usually employed, where a selective catalyst is in direct contact with a solution containing both glucose and oxygen. Through the selectivity of the catalyst, one fuel component is depleted at the electrode while the other component diffuses to the lower layers of the cell. An example for such a system is presented by Rapoport et al. [9], as reported above;

(3) A third option entails the use two selective catalysts, each only active towards one of the oxygen or glucose, respectively, such as some of the catalysts described above. This configuration usually requires no selective membrane.

FIGS. 4A-4G illustrate an exemplary fabrication process for manufacturing a miniaturized fuel cell design using semiconductor fabrication techniques as applied to the field of micro solid oxide fuel cells (μSOFCs). [8] The aim is to build a device based on a solid proton-conducting membrane, for example a hydrated metal oxide such as ceria. This technique is fully CMOS-compatible, and may be implemented on-chip together with sensor or bioelectronics devices, or built into the casing of an implant. Various fabrication process steps are depicted in cross-sectional views.

Returning to FIGS. 4A-4G, in FIG. 4A, substrate 30, for example a semiconductor material such as silicon or silicon oxide, is coated with first barrier layer 32 on a first side of the substrate 30 and with second barrier layer 34 on a second side of the substrate 30. The barrier layers 32 and 34 may be, for example, silicon nitride ("$Si_xN_y$") films deposited by a low pressure chemical vapor deposition process ("LPCVD") or similar techniques.

In FIG. 4B, a photoresist layer P is applied over second barrier layer 34, then patterned using a photolithographic process to expose portions 36 of the second barrier layer 34. For the photolithographic process, a protective layer may be formed over the photoresist layer, then patterned to expose the portions of the photoresist layer P to be removed. Generally, such a protective layer would be impervious to the photolithography process.

In FIG. 4C, a reactive ion etching (RIE) process is performed to remove the barrier layer material at exposed portions 36, thereby exposing portions 38 of the substrate 30.

After the RIE process is complete, the remaining photoresist layer P can be removed. In FIG. 4D, an anisotropic wet etching process, for example KOH etching, is performed at the exposed portions 38, creating cavities 31 and exposing portions 33 of the side of first barrier layer 32 that faces substrate 30.

In FIG. 4E, a thin film of metal oxide, for example, ceria, is deposited on the side of the first barrier layer 32 opposite the substrate 30, to form the electrolyte layer 35. Two example methods for the assembly of thin film membranes are the vacuum deposition technique pulsed laser deposition (PLD) and the wet-chemical deposition method of spray pyrolysis. PLD is a physical vapor deposition (PVD) method in which a high energy pulsed laser light source such as a KrF excimer laser is used to ablate a target material and deposit it on a substrate. PLD is well suited for the deposition of metal oxide thin films with a high degree of control over the chemical composition and microstructure. In spray pyrolysis, a solution of precursor salts and organics is sprayed via conventional spray painting systems on a heated substrate, which leads to an evaporation of the solvents and a thin film pyrolysis to the desired metal oxide. Spray pyrolysis and subsequent annealing offers great control over the microstructure, grain size and degree of crystallization of the film. In some embodiments, other techniques may be used to assemble the thin film metal oxide, such as, for example, a reactive magnetron sputtering deposition process or a radio frequency magnetron sputtering deposition process.

Spray pyrolysis typically creates microstructures with spherical or ellipsoidal grains, whereas PLD creates a columnar microstructure when amorphous substrates are used. This has immediate impact on the directionality of grain boundaries. Proton conductivity in ceria has been shown to operate along grain boundaries and adsorbed water on grain surfaces. [5] This means that for the purpose of cell membranes, the PLD films are expected to be beneficial for cross plane designs such as shown in FIG. 1. Without being bound to any particular theory, this is believed to be due to the fact that because of the columnar microstructure of a PLD film, most grain boundaries are aligned with the cross-plane direction of conduction. For instances where an in-plane design is desired, for example, as shown in FIGS. 9A-9D, the trend towards isotropy of the grain boundary orientations in sprayed films leads to an expected higher cross plane conductivity than the PLD films.

Furthermore, spray pyrolysis may lead to cost savings because it is readily scalable and does not require expensive equipment such as a high vacuum chamber or an excimer laser. Also, precursor materials can be used as-is, while in PLD, highly densified targets usually need to be pressed and sintered at high temperatures.

In FIG. 4F, a reactive ion etching process is performed to remove material of the first barrier layer 32 at exposed portions 33 in order to expose portions 35A of the electrolyte layer 35, and also to remove the remaining barrier layer 34.

In FIG. 4G, a cathode catalyst 37 is deposited on the portion of electrolyte layer 35A exposed by the etching away of portions 33. An anode catalyst 39 is deposited on the opposite side of electrolyte layer 35, for example platinum, to form two-chamber product fuel cell 310.

It should be noted that the exemplary fabrication process discussed above may include (and often does include) additional and/or alternate fabrication steps that are omitted here for convenience. For example, patterning of a particular material layer may include various deposition and etching steps. Also, additional structures may be formed at the shown layers and/or at various additional layers. In some cases, different deposition, patterning, or etching processes may be used. In some cases, different materials may be used.

With reference to FIGS. 9A-9D, it should be noted that similar fabrication processes can be used to produce alternative cross-plane and in-plane glucose fuel cell configurations. FIGS. 9A and 9B show cross-sectional views of exemplary in-plane configurations in which the cathodes and anodes are alternatingly formed on the surface of the electrolyte. FIGS. 9C and 9D show cross-sectional views of exemplary cross-plane configurations in which the cathodes and anodes are formed as offset layers on the same side of the substrate. With reference to FIGS. 10A-10C, similar fabrication processes can be used to produce folded or rolled-up glucose fuel cell configurations with both in-plane and cross-plane conduction pathways in which a fluid can flow through the voids between adjacent layers. FIG. 10A shows a cross-sectional view of a flexible cathode/electrolyte/anode stack that is rolled-up using a separation membrane to prevent contact between adjacent portions of cathode and anode. FIGS. 10B and 10C show cross-sectional views of exemplary in-plane configurations in which the cathodes and anodes are alternatingly formed on the surface of the electrolyte over a flexible substrate. In the exemplary embodiments shown in FIGS. 9A-9D and FIGS. 10A-10C, features sizes (e.g., electrode sizes, thicknesses, distance between electrodes, depth of trenches, etc.) may be between at least 10 nm to at most 10 μm.

Applications for the Fuel Cell

As disclosed above, using a solid electrolyte yields electrolytes at much smaller length scales than traditional membranes, e.g., from about 10 μm down to only about 10 nm, leading to significant performance enhancements in terms of power and energy density. This innovation can be used to provide glucose-operated fuel cell architectures to power biomedical applications that use only solid state materials and are integrated on silicon. With implantable glucose-operated fuel cells based on solid state materials and a proton conducting mechanism, higher power densities can be targeted when compared to standard, traditional polymer-based fuel cells. A key aspect is that both chemical reactants, glucose and oxygen, are abundant and available in the body fluids and can easily be transferred to electric power by the suggested solid state electrochemical cell on chip without the need for recharge or capacity restriction like in a battery, and the life-time of the novel solid state glucose-operated fuel cell is extended.

Figure 5:
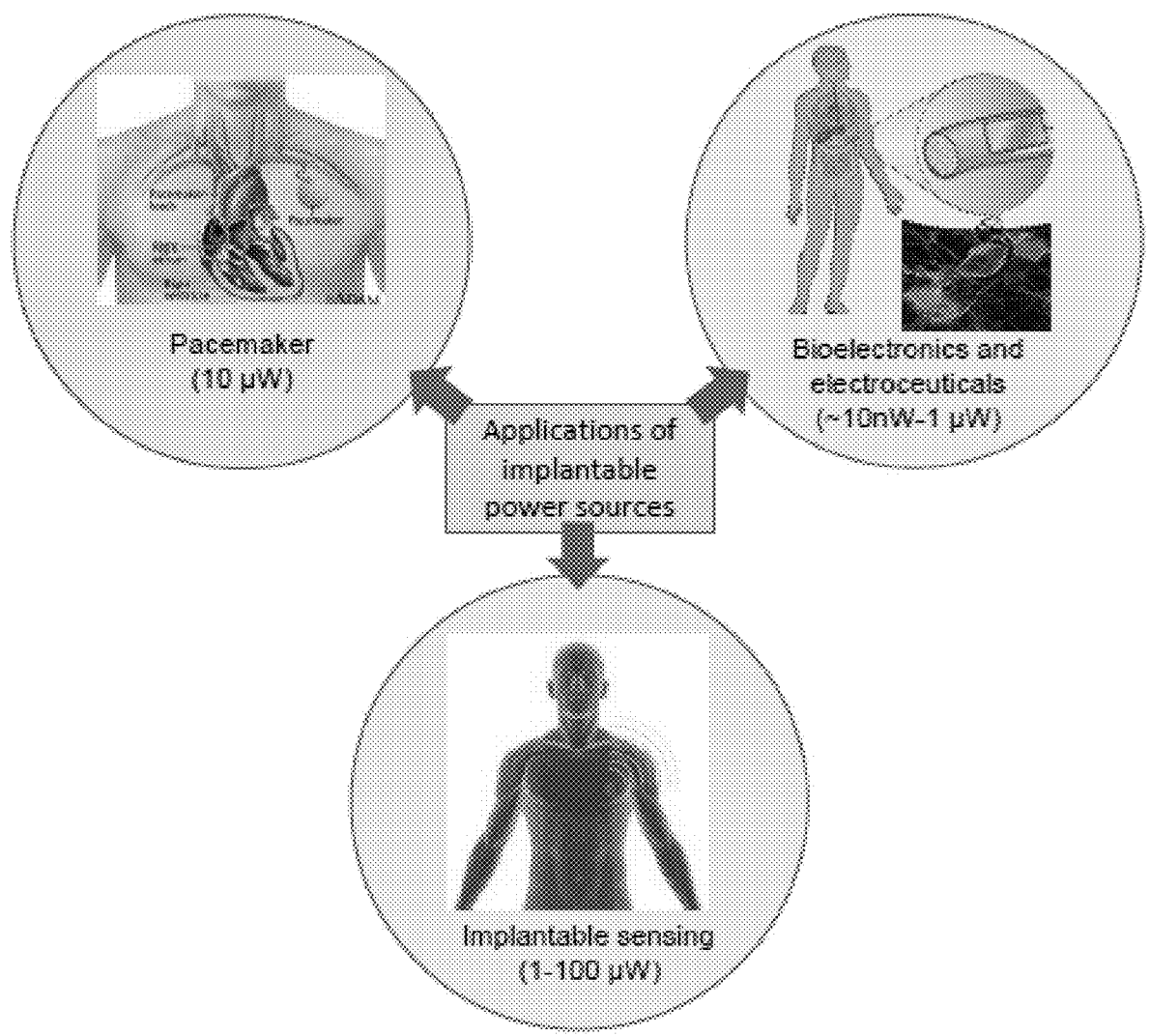
FIG. 5 illustrates example applications for implantable power sources powered by glucose fuel cells in accordance with exemplary embodiments.

Implantable glucose fuel cell systems can provide power to autonomous electronic medical devices for the human body. Usually, glucose-based fuel cells are useful in the conversion of chemical energy from a body fluid such as glucose and water to electrical energy. A prime application is to implement glucose fuel cells to miniaturized bioelectronics as long-term and small-scale power sources to increase future functionalities, as illustrated in FIG. 5. Here, a plethora of potential applications for glucose fuel cells can be envisioned. For example, implantable sensor systems that monitor certain physiological parameters related to chronic diseases and in some cases treat such chronic diseases could be powered by an on-chip fuel cell utilizing the glucose readily available in the human body. For instance, an implantable glucose monitor powered by a glucose fuel cell can include a sensor that monitors the cell voltage, which depends logarithmically on the glucose concentrations according to the Nernst equation and therefore may be used as a metric for blood glucose levels, thereby providing a robust and real-time sensor for glucose monitoring such as in diabetic patients. Such a glucose monitor may output glucose level readings and/or generate alerts based on glucose levels (e.g., if glucose level is above or below a predetermined threshold), and in some embodiments, the glucose monitor may include or control one or more pumps such as for administering insulin when a hyperglycemic condition is detected or for administering glucose when a hypoglycemic condition is detected.

Another application lies in powering implantable medical devices such as pacemakers or bioelectronic devices, which have primarily been powered by conventional batteries since the 1960's but would equally benefit from increased energy densities. Powering such devices with a glucose fuel cell could dispense with the need for a relatively bulkier battery that cannot be recharged and thus requires to be surgically replaced after being fully discharged. Devices may include a fuel cell that is used to provide electrical power to a rechargeable electrical storage device (e.g., battery or capacitor) such that power can continue for some amount of time after the glucose level in the fuel source falls below an operational threshold of the fuel cell (e.g., to allow the device to generate an alert or take other action).

It should be noted that devices of the type described herein may be configured to be partially implantable such that a first portion of the device is disposed within the body and a second portion of device is maintained outside of the body such as through the skin. In such a configuration, the anode can be disposed in the first portion such that the anode is exposed to a glucose-containing bodily fluid and the cathode can be disposed in the second portion such that the cathode is exposed to air outside of the body. In such devices, various types of operational and consumable elements can be maintained outside of the body, such as fluid pumps, fluid reservoirs, tubing, injection ports, battery, filters, etc. It is envisioned that a completely self-contained continuous glucose monitoring device can be produced that monitors glucose levels and delivers insulin and optionally glucose in order to manage diabetes, although alternative devices could be used to deliver virtually any type of medicine or supplement.

Moreover, the enhanced performance and energy density of the glucose fuel cells can find applications outside the biomedical arena. For example, a glucose fuel cell may serve as power unit for consumer electronics such as laptops and portable telephones. In areas where the electrical grid is either missing or hard to reach, all that is needed to power the device is an easy to procure solution of glucose. It should also be borne in mind that reactions other than the conversion of glucose to gluconic acid may power the fuel cell, provided that such reactions are amenable to applications in a fuel cell with a proton-conducting electrolyte. For instance, ethanol produced from glucose in fermentation tanks may be oxidized in fuel cells featuring abiotic catalysts, electroactive microorganisms, or enzymes that convert it to, for example, acetaldehyde and/or acetic acid, thereby providing a convenient, renewable power source for facilities where the glucose is fermented.

Example 1

Manufacturing a Ceria Electrolyte Cell

Hydrated ceria has been investigated as a proton conductor at or near room temperature. [4-6] It has been shown that at low temperatures of 70° C., this material has a conductivity of ~8.10-5 S cm$^{-1}$. [6] In addition, the conductivity tends to increase with decreasing temperature up to the lowest reported temperature of 70° C. While this is two or three orders of magnitude lower than state-of-the-art polymer electrolyte membranes such as Nafion, [7] the hypothesis was tested that lowered conductivity might be offset by reducing the conduction path length to only a few hundred nanometers.

This was achieved by fabricating free-standing solid electrolyte membranes in the following fashion. Silicon wafers 4 inches in diameter and 380 μm in thickness, double-side polished, orientation 100 (Sil'tronix, France) served as the initial substrate for the fabrication process. The silicon wafers were provided by the supplier with 200 nm silicon nitrite ($Si_xN_y$) barrier layers deposited on both sides of the substrate via low-pressure chemical vapor deposition. A photolithographic process was used to create an etching mask for reactive ion etching of the back side nitrite layer in the shape of squares. Reactive ion etching was then applied to open up square windows in the backside nitrite layer, and the wafer was then cut into smaller square samples having an area of 22.3×22.3 mm² for easier handling.

Next, anisotropic wet etching was performed to create cavities in the substrate silicon under the windows and exposing a portion of front side nitrite layer, thereby enabling the creation of free standing square membranes on the front side of the wafer. Thereafter, a ceria thin film of 250 nm thickness was deposited on the front side of the samples using pulsed laser deposition (PLD). The film was deposited at a temperature of 400° C. and under at atmosphere of $2.6·10^{-2}$ mbar of oxygen. The laser energy was 154 mJ on the target, at a repetition rate of 10 Hz, and the substrate was at a distance of 70 mm away from the target.

Figure 6:
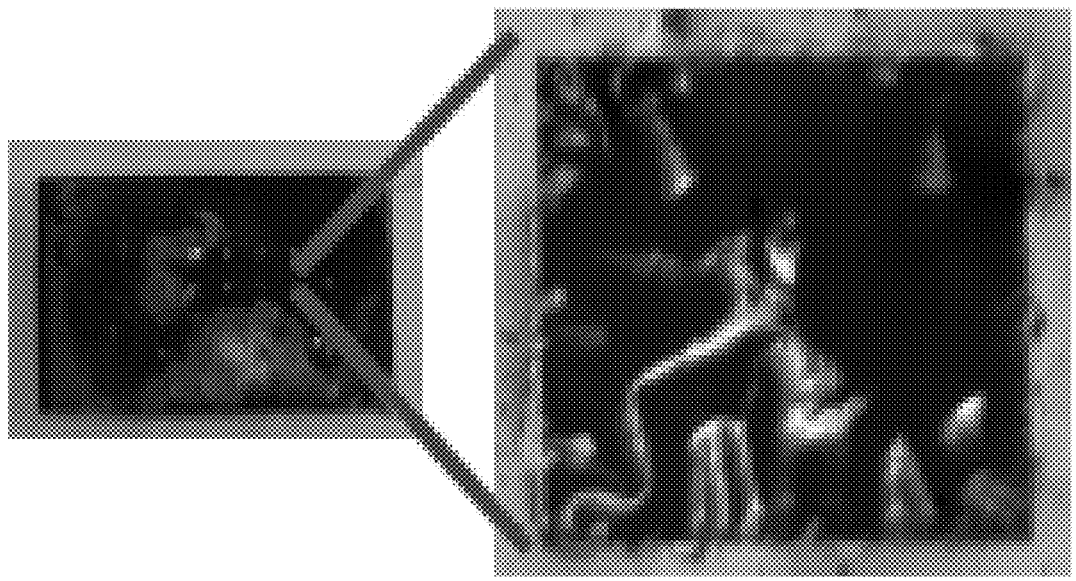
FIG. 6 includes a photograph of an assembled fuel cell chip featuring 36 free-standing ceria ceramic membranes and an optical micrograph of one of the membranes in accordance with one exemplary embodiment.
Figure 7A:
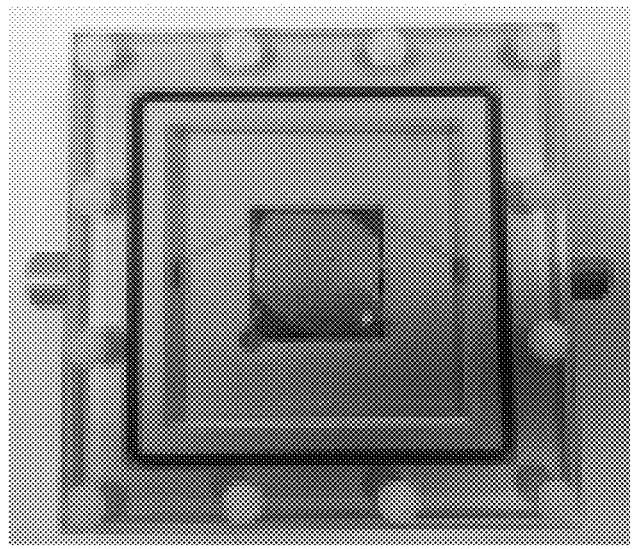
FIG. 7A is a photograph of a fuel cell placed inside a custom-designed flow case.
Figure 7B:
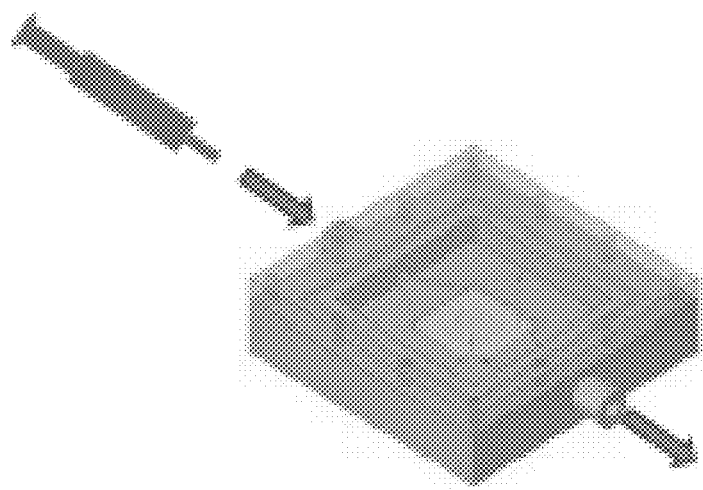
FIG. 7B is a schematic of the operation of the fuel cell inside the flow case under a continuous liquid flow using a syringe pump in accordance with one exemplary embodiment.

Subsequently, a second reactive ion etching step was carried out from the backside of the samples to remove the portion of the front side nitride layer previously exposed by the wet etching and to leave a free standing ceramic membrane of ceria. Finally, 20 nm of Pt were deposited on both sides of the samples using electron beam evaporation at room temperature. To hydrate the ceria ceramic membranes, the samples were placed over a bath of deionized water at 85° C. for 5 hours. FIG. 6 shows a photograph of the assembled product fuel cell chip as well as an optical micrograph of a free-standing ceria ceramic membrane. As illustrated in FIG. 7A, the chip was placed inside a custom-designed flow case (not shown: the bottom of the fuel cell was open to ambient air). FIG. 7B is a schematic of the operation of the fuel cell inside the flow case under a continuous liquid flow using a syringe pump.

Example 2

Testing the Ceria Electrolyte Cell

Two sets of experiments were carried out with different samples to test the cell of Example 1. In both cases, a solution of glucose having a concentration of 1 M in phosphate buffered saline (PBS) served as the anode side fuel. PBS served to emulate the pH value and ion composition of human blood.

Figure 8:
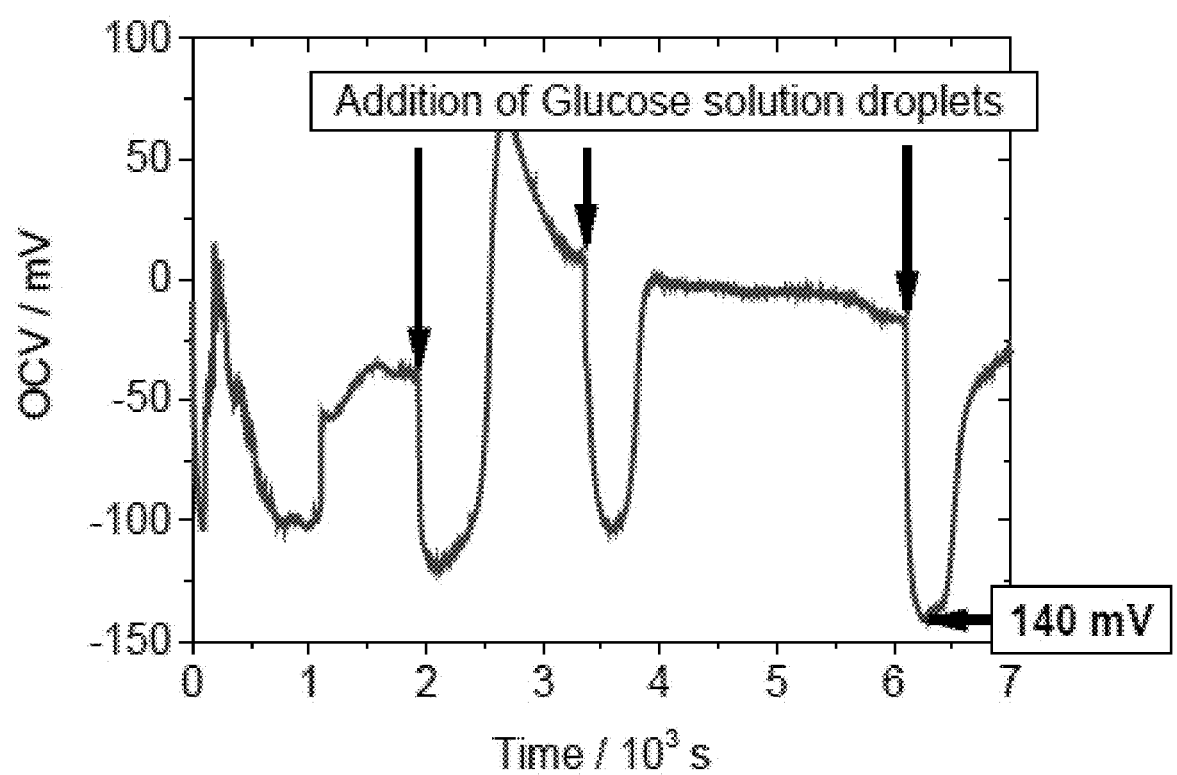
FIG. 8 is a graph showing the open circuit voltage of a glucose fuel cell as a function of time in accordance with one exemplary embodiment.

In the first set of experiments, droplets of glucose solution were deposited on the top, anode side of the sample chip using a syringe, and the back, cathode side was left open to ambient air. As a result, the oxygen in the air served as the oxidizer. The chip was contacted to a digital source measurement unit at the front and back side using gold needles. The open circuit potential of the thus assembled electrochemical cell was measured at room temperature (25° C.). FIG. 8 shows the open circuit voltage (OCV) of the cell as a function of time. At each of the marked spots, glucose solution was added to the surface, and one can see that immediately after glucose solution was added, the open circuit potential spiked. The peak open circuit potential obtained in this experiment was 140 mV. After a peak in the OCV was reached, the voltage decayed rapidly and even changed polarity, which is likely due to backward reaction of the reaction products. The decay in OCV is believed to be due to evaporation of the water in the glucose solution.

The two series of experiments show that the prototype of Example 1 was indeed working as a fuel cell with a useful OCV. In both cases, the cell showed activity in the presence of a glucose solution. Furthermore, in the absence of glucose in the fuel solution, no open circuit voltage was measured, clearly indicating that the measured electrochemical potential was due to glucose oxidation. Taken together, these results show that product-conducting metal oxides can be used as electrolytes in glucose fuel cells operating at temperatures as low as that of the human body.

While some exemplary embodiments are described herein using cross-sectional views of exemplary devices, it will be apparent to a skilled artisan, using the teachings of the present patent application, that the described structures and fabrication processes apply to three-dimensional structures and fabrication processes. Thus, for example, with reference to FIGS. 9A-9D and FIGS. 10A-10C, where a single row of alternating anodes and cathodes may be shown, an actual device may have an array or grid or other arrangement of alternating anodes and cathodes. The concepts discussed herein allow for a wide range of device configurations.

The embodiments of the invention described above are intended to be merely exemplary; numerous variations and modifications will be apparent to those skilled in the art. All such variations and modifications are intended to be within the scope of the present invention as defined in any appended claims.

What is claimed is:

1. A device comprising a glucose fuel cell, the glucose fuel cell comprising:
    an anode configured to oxidize glucose;
    a cathode configured to reduce an oxidant;
    a proton-conducting metal oxide electrolyte comprising a metal oxide material in the form of a proton-conducting metal oxide layer interposed between and in contact with the anode and the cathode;
    a substrate; and
    a glucose sensor configured to output a glucose level signal based on a voltage of the glucose fuel cell,
    wherein:
    the proton conducting metal oxide layer is provided on a first surface of the substrate, the metal oxide layer having a first metal oxide layer surface facing the substrate and a second metal oxide layer surface facing away from the substrate,
    a cavity is etched on a second surface of the substrate to expose a portion of the first metal oxide layer surface, and
    one of: (i) the anode is formed on a portion of the first metal oxide layer surface and the cathode is formed on a portion of the second metal oxide layer surface; or (ii) the anode is formed on a portion of the second metal oxide layer surface and the cathode is formed on a portion of the first metal oxide layer surface.

2. The device of claim 1, where the metal oxide material is one of:
    $CeO_2$;
    $CeO_2$ doped with at least one rare earth element;
    a perovskite oxide of the form $ABO_3$;
    an oxide selected from group consisting of $SrTiO_3$, $SrZrO_3$, $BaCeO_3$, $BaZrO_3$, $BaTiO_3$, $BaTbO_3$, $BaThO_3$, $SrCeO_3$, $CaZrO_3$, $LaScO_3$, $LaErO_3$, $KTaO_3$, and combinations thereof;
    a perovskite oxide of the form $ABO_3$ doped with an element selected from the group consisting of Y, Sc, In, Gd, Sr, Hf, Ce, Ca, Zr, Sm and combinations thereof;
    a perovskite oxide of the form $ABO_3$ that is hydrated;
    a metal oxide selected from the group consisting of $SrCe_{1-x}Yb_xO_3$, where x is from at least 0 to at most 1, $LaY_{1-x}Zn_xO_3$, where x is from at least 0 to at most 1, $Sr_2(GaNb)O_6$; $Ba_3CaNb_2O_9$, $ZrO_2$, and $ZrO_2$ doped with at least one rare earth element;
    a biocompatible metal oxide;
    an amorphous metal oxide;
    a polycrystalline metal oxide;

a nanocrystalline metal oxide; or a biphasic amorphous to nanocrystalline metal oxide.

3. The device of claim 1, where the electrolyte has a thickness from at least 10 nm to at most 10 μm.

4. The device of claim 1, where the oxidation of the glucose is catalyzed by one or more of:
an abiotic catalyst;
an enzyme;
a living cell;
a catalyst selected from the group consisting of platinum, nanostructured platinum, platinum alloys, platinum-ruthenium, platinum-bismuth, platinum-tungsten, Raney-platinum, ceria-platinum, ceria-nickel, gold-platinum, gold-palladium, ceria-gold, rhodium, iridium, and combinations thereof; or
the metal oxide material.

5. The device of claim 1, where at least one of:
the oxidant is oxygen;
the reduction of the oxidant is catalyzed by one or more of a carbon nanotube supported catalyst, activated carbon, palladium, Raney-platinum, or silver;
the glucose fuel cell is configured to oxidize glucose from a bodily fluid;
the glucose fuel cell is configured to oxidize glucose from blood;
the device is configured to be at least partially implanted in a vertebrate.

6. The device of claim 1, further comprising one of:
an electrical storage device coupled to the glucose fuel cell for storage of electrical power from the glucose fuel cell; or
a rechargeable battery coupled to the glucose fuel cell for storage of electrical power from the glucose fuel cell.

7. The device of claim 1, wherein the anode and cathode are arranged in one of:
an in-plane configuration;
a cross-plane configuration;
a folded configuration; or
a rolled-up configuration.

8. The device of claim 1, wherein the glucose level signal is related logarithmically to the voltage of the glucose fuel cell according to the Nernst equation.

9. The device of claim 1, further comprising at least one of:
a pump configured to pump insulin based on the glucose level signal; or
a pump configured to pump at least one fluid other than insulin based on the glucose level signal.

10. The invention of claim 1, wherein the metal oxide material is a biocompatible metal oxide having a proton conductivity of at least $8 \cdot 10^{-5}$ S cm$^{-1}$ at temperatures in the range of 20° C. to 45° C.

11. The device of claim 1, where the substrate includes a substrate layer and a first barrier layer on the substrate layer, and where the metal oxide layer is on the first barrier layer.

12. The device of claim 1, where the cathode comprises a first abiotic catalyst and the anode comprises a second abiotic catalyst.

13. A device comprising a glucose fuel cell, the glucose fuel cell comprising:
a substrate;
a proton-conducting metal oxide layer on a first surface of the substrate, the metal oxide layer having a first metal oxide layer surface facing the substrate and a second metal oxide layer surface facing away from the substrate;
a cavity etched on a second surface of the substrate to expose a portion of the first metal oxide layer surface;
an anode configured to oxidize glucose formed on a portion of the second metal oxide layer surface; and
a cathode configured to reduce an oxidant formed on the portion of the first metal oxide layer surface,
wherein the proton-conducting metal oxide layer forms a proton-conducting metal oxide electrolyte interposed between and in contact with the anode and the cathode.

14. The device of claim 13, where the substrate includes a substrate layer and a first barrier layer on the substrate layer, and where the metal oxide layer is on the first barrier layer.

15. The device of claim 13, where the cathode comprises a first abiotic catalyst and the anode comprises a second abiotic catalyst.

16. The device of claim 13, where the metal oxide material is one of:
$CeO_2$;
$CeO_2$ doped with at least one rare earth element;
a perovskite oxide of the form $ABO_3$;
an oxide selected from group consisting of $SrTiO_3$, $SrZrO_3$, $BaCeO_3$, $BaZrO_3$, $BaTiO_3$, $BaTbO_3$, $BaThO_3$, $SrCeO_3$, $CaZrO_3$, $LaScO_3$, $LaErO_3$, $KTaO_3$, and combinations thereof;
a perovskite oxide of the form $ABO_3$ doped with an element selected from the group consisting of Y, Sc, In, Gd, Sr, Hf, Ce, Ca, Zr, Sm and combinations thereof;
a perovskite oxide of the form $ABO_3$ that is hydrated;
a metal oxide selected from the group consisting of $SrCe_{1-x}Yb_xO_3$, where x is from at least 0 to at most 1, $LaY_{1-x}Zn_xO_3$, where x is from at least 0 to at most 1, $Sr_2(GaNb)O_6$; $Ba_3CaNb_2O_9$, $ZrO_2$, and $ZrO_2$ doped with at least one rare earth element;
a biocompatible metal oxide;
an amorphous metal oxide;
a polycrystalline metal oxide;
a nanocrystalline metal oxide; or
a biphasic amorphous to nanocrystalline metal oxide.

17. The device of claim 13, where the electrolyte has a thickness from at least 10 nm to at most 10 μm.

18. The device of claim 13, where the oxidation of the glucose is catalyzed by one or more of:
an abiotic catalyst;
an enzyme;
a living cell;
a catalyst selected from the group consisting of platinum, nanostructured platinum, platinum alloys, platinum-ruthenium, platinum-bismuth, platinum-tungsten, Raney-platinum, ceria-platinum, ceria-nickel, gold-platinum, gold-palladium, ceria-gold, rhodium, iridium, and combinations thereof; or
the metal oxide material.

19. The device of claim 13, where at least one of:
the oxidant is oxygen;
the reduction of the oxidant is catalyzed by one or more of a carbon nanotube supported catalyst, activated carbon, palladium, Raney-platinum, or silver;
the glucose fuel cell is configured to oxidize glucose from a bodily fluid;
the glucose fuel cell is configured to oxidize glucose from blood;
the device is configured to be at least partially implanted in a vertebrate.

20. The device of claim 13, further comprising one of:
an electrical storage device coupled to the glucose fuel cell for storage of electrical power from the glucose fuel cell; or
a rechargeable battery coupled to the glucose fuel cell for storage of electrical power from the glucose fuel cell.

21. The device of claim 13, wherein the anode and cathode are arranged in one of:
an in-plane configuration;
a cross-plane configuration;
a folded configuration; or
a rolled-up configuration.

22. The device of claim 13, further comprising:
a glucose sensor configured to output a glucose level signal based on a voltage of the glucose fuel cell.

23. The device of claim 22, wherein the glucose level signal is related logarithmically to the voltage of the glucose fuel cell according to the Nernst equation.

24. The device of claim 22, further comprising at least one of:
a pump configured to pump insulin based on the glucose level signal; or
a pump configured to pump at least one fluid other than insulin based on the glucose level signal.

25. A device comprising a glucose fuel cell, the glucose fuel cell comprising:
a substrate;
a proton conducting metal oxide layer on a first surface of the substrate, the metal oxide layer having a first metal oxide layer surface facing the substrate and a second metal oxide layer surface facing away from the substrate;
a cavity etched on a second surface of the substrate to expose a portion of the first metal oxide layer surface;
an anode configured to oxidize glucose formed on the portion of the first metal oxide layer surface; and
a cathode configured to reduce an oxidant formed on a portion of the second metal oxide layer surface,
wherein the proton-conducting metal oxide layer forms a proton-conducting metal oxide electrolyte interposed between and in contact with the anode and the cathode.

26. The device of claim 25, where the substrate includes a substrate layer and a first barrier layer on the substrate layer, and where the metal oxide layer is on the first barrier layer.

27. The device of claim 25, where the cathode comprises a first abiotic catalyst and the anode comprises a second abiotic catalyst.

28. The device of claim 25, where the metal oxide material is one of:
CeO2;
CeO2 doped with at least one rare earth element;
a perovskite oxide of the form ABO3;
an oxide selected from group consisting of SrTiO3, SrZrO3, BaCeO3, BaZrO3, BaTiO3, BaTbO3, BaThO3, SrCeO3, CaZrO3, LaScO3, LaErO3, KTaO3, and combinations thereof;
a perovskite oxide of the form ABO3 doped with an element selected from the group consisting of Y, Sc, In, Gd, Sr, Hf, Ce, Ca, Zr, Sm and combinations thereof;
a perovskite oxide of the form ABO3 that is hydrated;
a metal oxide selected from the group consisting of SrCe1-xYbxO3, where x is from at least 0 to at most 1, LaY1-xZnxO3, where x is from at least 0 to at most 1, Sr2(GaNb)O6; Ba3CaNb2O9, ZrO2, and ZrO2 doped with at least one rare earth element;
a biocompatible metal oxide;
an amorphous metal oxide;
a polycrystalline metal oxide;
a nanocrystalline metal oxide; or
a biphasic amorphous to nanocrystalline metal oxide.

29. The device of claim 25, where the electrolyte has a thickness from at least 10 nm to at most 10 µm.

30. The device of claim 25, where the oxidation of the glucose is catalyzed by one or more of:
an abiotic catalyst;
an enzyme;
a living cell;
a catalyst selected from the group consisting of platinum, nanostructured platinum, platinum alloys, platinum-ruthenium, platinum-bismuth, platinum-tungsten, Raney-platinum, ceria-platinum, ceria-nickel, gold-platinum, gold-palladium, ceria-gold, rhodium, iridium, and combinations thereof; or
the metal oxide material.

31. The device of claim 25, where at least one of:
the oxidant is oxygen;
the reduction of the oxidant is catalyzed by one or more of a carbon nanotube supported catalyst, activated carbon, palladium, Raney-platinum, or silver;
the glucose fuel cell is configured to oxidize glucose from a bodily fluid;
the glucose fuel cell is configured to oxidize glucose from blood;
the device is configured to be at least partially implanted in a vertebrate.

32. The device of claim 25, further comprising one of:
an electrical storage device coupled to the glucose fuel cell for storage of electrical power from the glucose fuel cell; or
a rechargeable battery coupled to the glucose fuel cell for storage of electrical power from the glucose fuel cell.

33. The device of claim 25, wherein the anode and cathode are arranged in one of:
an in-plane configuration;
a cross-plane configuration;
a folded configuration; or
a rolled-up configuration.

34. The device of claim 25, further comprising:
a glucose sensor configured to output a glucose level signal based on a voltage of the glucose fuel cell.

35. The device of claim 34, wherein the glucose level signal is related logarithmically to the voltage of the glucose fuel cell according to the Nernst equation.

36. The device of claim 34, further comprising at least one of:
a pump configured to pump insulin based on the glucose level signal; or
a pump configured to pump at least one fluid other than insulin based on the glucose level signal.

* * * * *